(12) United States Patent
Rantala et al.

(10) Patent No.: US 6,963,767 B2
(45) Date of Patent: Nov. 8, 2005

(54) PULSE OXIMETER

(75) Inventors: Borje Rantala, Helsinki (FI); Erno Muuranta, Helsinki (FI); Markku Spoof, Jokela (FI); Matti Huiku, Espoo (FI)

(73) Assignee: GE Healthcare Finland Oy, Helsinki (FI)

( * ) Notice: Subject to any disclaimer, the term of this patent is extended or adjusted under 35 U.S.C. 154(b) by 184 days.

(21) Appl. No.: 10/136,956

(22) Filed: May 2, 2002

(65) Prior Publication Data

US 2002/0198442 A1 Dec. 26, 2002

(30) Foreign Application Priority Data

Jul. 3, 2001 (EP) .............................................. 0166082

(51) Int. Cl.[7] .............................................. A61B 5/00
(52) U.S. Cl. ...................................... 600/336; 600/323
(58) Field of Search .............................. 600/309–310, 600/322–323, 330, 336

(56) References Cited

U.S. PATENT DOCUMENTS

| 4,942,877 A | 7/1990 | Sakai et al. |
| 5,919,134 A | * 7/1999 | Diab ........................ 600/323 |
| 5,995,858 A | 11/1999 | Kinast ....................... 600/323 |
| 2003/0028357 A1 | * 2/2003 | Norris et al. ............... 702/189 |

FOREIGN PATENT DOCUMENTS

| WO | WO99/52420 | 10/1999 | ............ A61B/5/00 |
| WO | WO 02/41536 | 5/2002 | ........... H04B/15/00 |

* cited by examiner

Primary Examiner—Mary Beth Jones
Assistant Examiner—Matthew Kremer
(74) Attorney, Agent, or Firm—Marsh Fischmann & Breyfogle LLP

(57) ABSTRACT

The invention relates to pulse oximeters used to measure blood oxygenation. The current trend towards lower power consumption has brought a problem of erroneous readings caused by intrachannel crosstalk, i.e. errors due to the coupling of undesired capacitive, inductive, or conductive (resistive) pulse power from the emitting side of the pulse oximeter directly to the detecting side of the oximeter. The pulse oximeter of the invention is therefore provided with means for detecting whether intrachannel crosstalk is present and whether it will cause erroneous results in the oxygenation measurements. The pulse oximeter is preferably further provided with means for eliminating intrachannel crosstalk which are adapted to control the measurement so that measurement signals can be obtained which are substantially void of crosstalk components.

41 Claims, 5 Drawing Sheets

PULSE OXIMETER

FIELD OF THE INVENTION

The invention relates generally to devices used for non-invasively determining the amount of at least one light absorbing substance in a subject. These devices are typically pulse oximeters used to measure blood oxygenation of a patient. More specifically, the invention relates to the detection of crosstalk in such devices and to such devices provided with means for detecting crosstalk. The invention further relates to such devices provided with means for eliminating the crosstalk. As discussed below, crosstalk here refers to direct electric crosstalk occuring within a single measuring channel.

BACKGROUND OF THE INVENTION

Pulse oximetry is at present the standard of care for the continuous monitoring of arterial oxygen saturation ($SpO_2$). Pulse oximeters provide instantaneous in-vivo measurements of arterial oxygenation, and thereby provide early warning of arterial hypoxemia, for example.

A pulse oximeter comprises a computerized measuring unit and a probe attached to the patient, typically to his or her finger or ear lobe. The probe includes a light source for sending an optical signal through the tissue and a photo detector for receiving the signal after transmission through the tissue. On the basis of the transmitted and received signals, light absorption by the tissue can be determined. During each cardiac cycle, light absorption by the tissue varies cyclically. During the diastolic phase, absorption is caused by venous blood, tissue, bone, and pigments, whereas during the systolic phase there is an increase in absorption, which is caused by the influx of arterial blood into the tissue. Pulse oximeters focus the measurement on this arterial blood portion by determining the difference between the peak absorption during the systolic phase and the constant absorption during the diastolic phase. Pulse oximetry is thus based on the assumption that the pulsatile component of the absorption is due to arterial blood only.

Light transmission through an ideal absorbing sample is determined by the known Lambert-Beer equation as follows:

$$I_{out} = I_{in} e^{-\epsilon DC}, \qquad (1)$$

where $I_{in}$ is the light intensity entering the sample, $I_{out}$ is the light intensity received from the sample, D is the path length through the sample, $\epsilon$ is the extinction coefficient of the analyte in the sample at a specific wavelength, and C is the concentration of the analyte. When $I_{in}$, D, and $\epsilon$ are known, and $I_{out}$ is measured, the concentration C can be calculated.

In pulse oximetry, in order to distinguish between the two species of hemoglobin, oxyhemoglobin ($HbO_2$), and deoxyhemoglobin (RHb), absorption must be measured at two different wavelengths, i.e. the probe includes two different light emitting diodes (LEDs). The wavelength values widely used are 660 nm (red) and 940 nm (infrared), since the said two species of hemoglobin have substantially different absorption values at these wavelengths. Each LED is illuminated in turn at a frequency which is typically several hundred Hz.

The accuracy of a pulse oximeter is affected by several factors. This is discussed briefly in the following.

Firstly, the dyshemoglobins which do not participate in oxygen transport, i.e. methemoglobin (MetHb) and carboxyhemoglobin (CoHb), absorb light at the wavelengths used in the measurement. Pulse oximeters are set up to measure oxygen saturation on the assumption that the patient's blood composition is the same as that of a healthy, non-smoking individual. Therefore, if these species of hemoglobin are present in higher concentrations than normal, a pulse oximeter may display erroneous data.

Secondly, intravenous dyes used for diagnostic purposes may cause considerable deviation in pulse oximeter readings. However, the effect of these dyes is short-lived since the liver purifies blood efficiently.

Thirdly, coatings such as nail polish may in practice impair the accuracy of a pulse oximeter, even though the absorption caused by them is constant, not pulsatile, and thus in theory it should not have an effect on the accuracy.

Fourthly, the optical signal may be degraded by both noise and motion artifacts. One source of noise is the ambient light received by the photodetector. Many solutions have been devised with the aim of minimizing or eliminating the effect of the movement of the patient on the signal, and the ability of a pulse oximeter to function correctly in the presence of patient motion depends on the design of the pulse oximeter. One way of canceling out the motion artefact is to use an extra wavelength for this purpose.

A further factor affecting the accuracy of a pulse oximeter is the direct electrical crosstalk between the circuitry driving the LEDs and the circuitry receiving the signal from the photodetector. Due to crosstalk of this type, non-optical signal components may superimpose on the signal received and thus cause erroneous oxygen saturation readings. This problem does not exist with conventional pulse oximeters using wide pulses, but has surfaced with the current trend towards lower power consumption, which is essential for battery operated oximeters, for example. Lower power consumption calls for narrower pulses for driving the LEDs, the narrower pulses being more vulnerable to this type of crosstalk. The problem is further aggravated if the tissue of the patient is thicker than normal, whereby the signal received from the photodetector is weaker than normal.

It is an objective of the invention to bring about a solution by means of which it is possible to decide whether this type of crosstalk is present and whether it will cause erroneous results in the oxygen saturation measurements. A further objective of the present invention is to bring about a solution by means of which the measurement can be performed so that the crosstalk, even if strong, will not cause erroneous readings.

SUMMARY OF THE INVENTION

These and other objectives of the invention are accomplished in accordance with the principles of the present invention by providing a pulse oximeter with means for detecting, in connection with each measurement, the presence of crosstalk. As mentioned above, the term "crosstalk" refers in this context to electric intrachannel crosstalk, i.e. to direct capacitive, inductive, or conductive (resistive) coupling of power from the circuitry driving the LEDs to the circuitry receiving the signal from the photodetector.

In its basic embodiment the pulse oximeter of the invention comprises means for detecting the presence of crosstalk. Thus, in the basic embodiment of the invention the user is only warned of the presence of crosstalk, and the crosstalk is not removed in the pulse oximeter, at least not automatically. This arises from the fact that the nature of crosstalk can be such that automatic elimination is not possible, but rather user action is required for reducing the amount of crosstalk. Furthermore, the detection of crosstalk can be used for purposes which are not directly related to the reduction of crosstalk, such as detecting a faulty probe or determining whether the cable type is suitable for the measurement.

However, in a preferred embodiment the detection process is used for eliminating the effect of crosstalk on the measurement results whenever this is possible. In other words, in a preferred embodiment of the invention the crosstalk is first detected and then removed. As discussed below, the removal may be realized in many ways. In some instances, however, the crosstalk may be so severe that correct results cannot be obtained, whereby the user is warned of the situation.

The pulse oximeter may also automatically reconfigure itself or advise the user to reconfigure the measurement arrangement, e.g. change the type of cable used, in order to reduce the amount of crosstalk.

Other features and advantages of the invention will become apparent by reference to the following detailed description and accompanying drawings.

BRIEF DESCRIPTION OF THE DRAWINGS

In the following, the invention and its preferred embodiments are described more closely by referring to the examples shown in FIGS. 1 to 10 in the appended drawings, wherein.

DETAILED DESCRIPTION OF THE INVENTION

Figure 1:
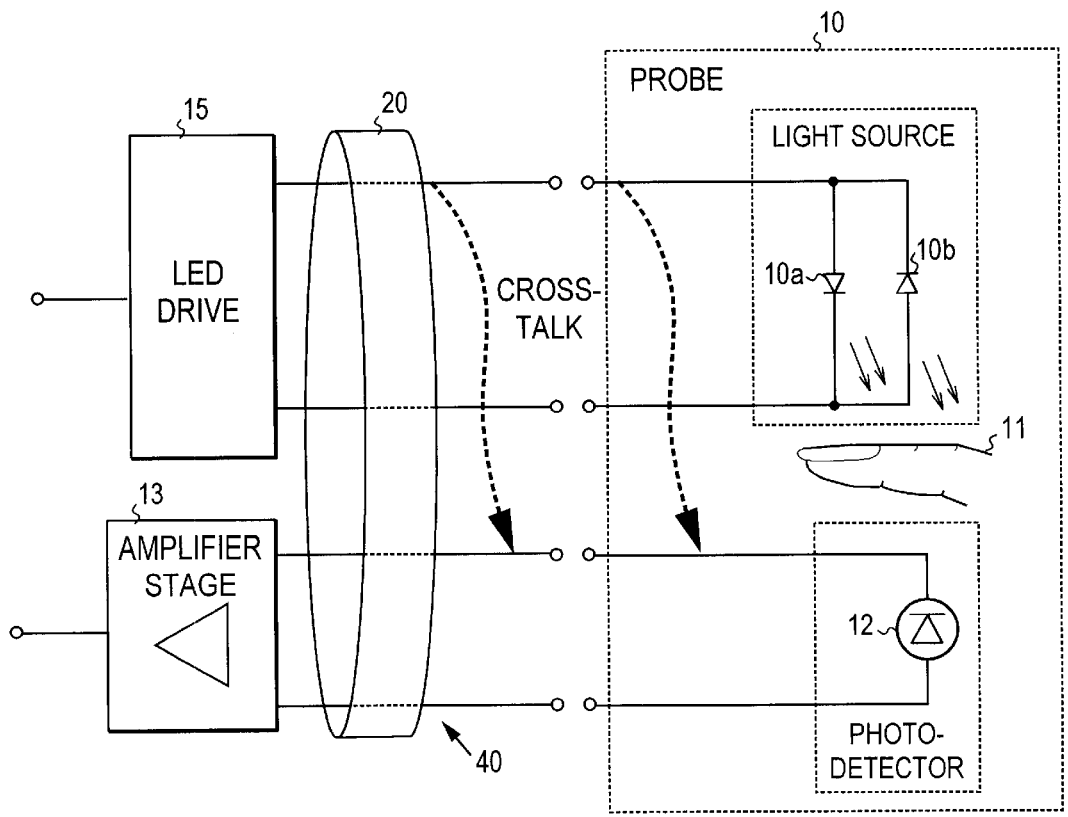
FIG. 1 illustrates the mechanism of crosstalk generation in a standard pulse oximeter.

FIG. 1 illustrates the mechanism of intrachannel crosstalk generation in a standard pulse oximeter. Light from two LEDs 10a and 10b, each operating at a respective wavelength, passes into patient tissue, such as a finger 11. The light propagated through or reflected from the tissue is received by a photodetector 12, which converts the optical signal received into an electrical signal and feeds it to an amplifier stage 13. The amplified signal is then supplied to a control unit (not shown in the figure), which carries out the processing of the signal received. The control unit further controls the LED drive 15 to alternately activate the LEDs. As mentioned above, each LED is typically illuminated several hundred times in a second. Crosstalk here refers to the undesired capacitive, inductive, or conductive (resistive) coupling of pulse power from the LED drive 15 to the circuitry 40 receiving the signal from the photodetector. Thus, the signal received by the control unit is a combination of the actual detector signal, noise, and crosstalk from the LED drive. The characteristics of the crosstalk depend on various items relating to the transmission path between the probe and the apparatus, such as the characteristics of the cable 20 and connectors used, and of the probe setup. Crosstalk is therefore variable in an unpredictable fashion.

Figure 2A:
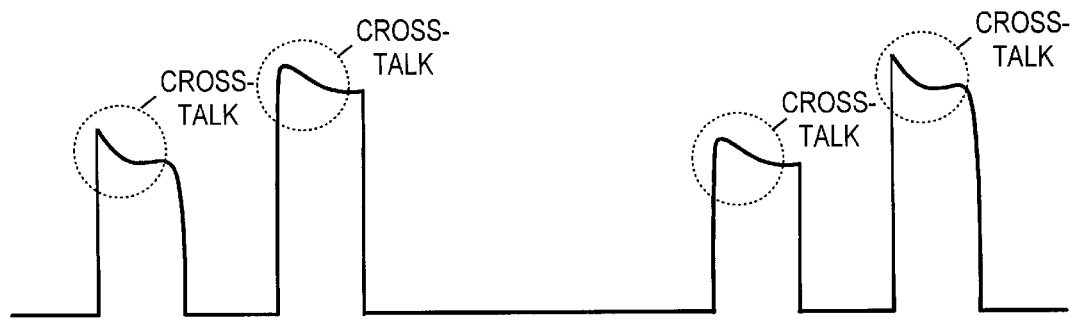
FIGS. 2a to 2c illustrate how crosstalk appears in oximeter signals.
Figure 2B:
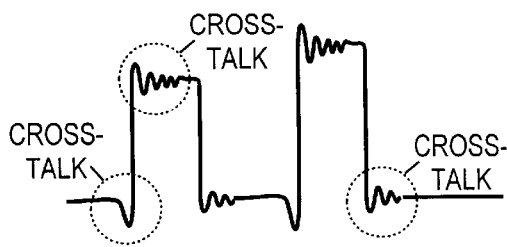

Crosstalk sets a lower limit for the acceptable signal level, as it is frequently larger than the noise and synchronous to the operation of the LED drive. It is normally capacitive in nature and largest at signal sections with the highest slew rate, i.e. at signal edges. As shown in FIGS. 2a and 2b, capacitive/inductive crosstalk appears typically as an overshoot or ringing at the leading edges of the pulses driving the LEDs. A similar undershoot can be seen at the trailing edges. The duration of the overshoot, which is often exponentially decreasing, is variable and depends mainly on the cabling capacitance between the electronics and the probe. In some cabling configurations, crosstalk can appear as ringing at all signal edges.

Figure 2C:
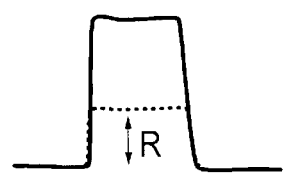

A further type of crosstalk is resistive crosstalk caused by a leakage resistance connecting pulse energy to the receiving circuitry. Especially when the oximeter cable 20 consists of two parts, typically a longer trunk cable and a shorter probe cable, moisture and dirt in the connectors will cause such a resistance and thus resistive crosstalk. As shown in FIG. 2c, resistive crosstalk (denoted by the letter R) causes amplitude changes rather than pulse deformation. The sign of the error caused by resistive crosstalk (i.e. the sign of the component R) depends typically on the polarity of the driving pulses. Resistive crosstalk can therefore increase the DC level of the red signal and decrease the DC level of the infrared signal, or vice versa, which in turn causes error to the measurement.

Figure 3:
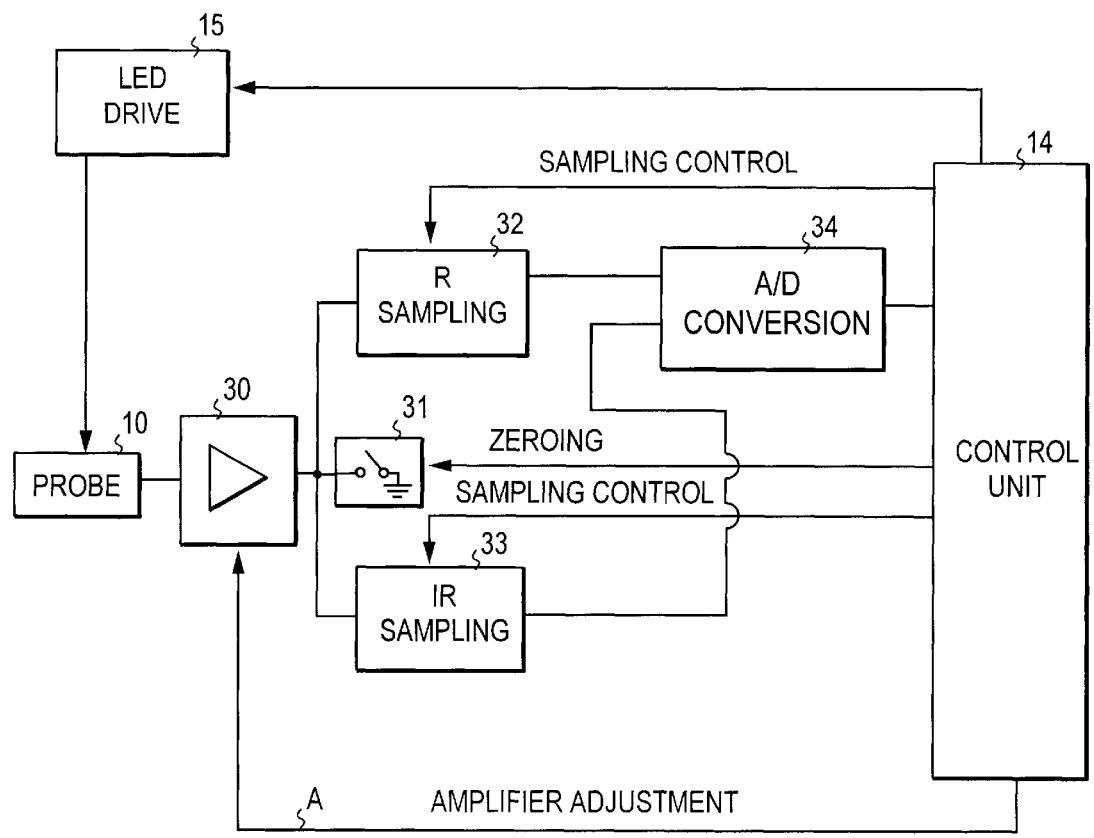
FIG. 3 shows a pulse oximeter according to one embodiment of the invention.

FIG. 3 is a block diagram of one embodiment of a pulse oximeter according to the present invention. This embodiment is based on a traditional pulse oximeter where synchronous detection is used. The control unit 14 activates the LEDs alternately by controlling the LED drive 15. The signal received from the probe 10 (i.e. photodetector) is supplied to an amplifier stage 30, typically including several successive amplifiers, such as a preamplifier (which performs a preamplification), an AC coupled amplifier (which filters interference caused by DC light), and a controllable amplifier (which amplifies the signal to a level suitable for subsequent analog-digital conversion). After the amplifier stage, an analog switch 31, controlled by the control unit, ensures that the signal is zeroed between consecutive pulses. The reception branch is then divided into two branches: the IR branch for the infrared signal and the R branch for the red signal. Each branch is preceded by an analog switch (not shown in the figure) which is controlled by the control unit so that the pulses are connected to their respective branch (the R pulses to the R branch and the IR pulses to the IR branch). In each branch a sampling unit (32, 33) then takes samples of the pulses received by the branch. The control unit controls the R sampling unit so that it samples the R pulses and the IR sampling unit so that it samples the IR pulses. The sampling units typically include a sampling switch and a capacitor which is charged to the pulse voltage prevailing at the sampling moment. The sampled signals are then supplied to an A/D converter 34 which converts them into digitized format for the control unit.

Figure 4:
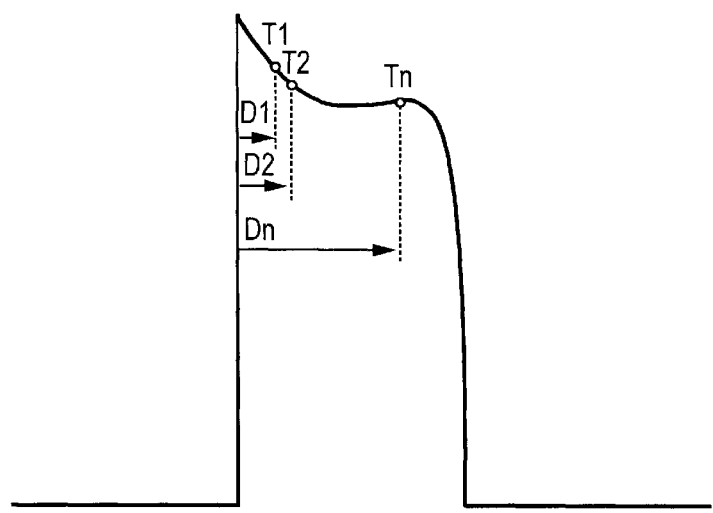
FIG. 4 illustrates the principle of crosstalk detection in the embodiment of FIG. 3.

In order to detect the presence of capacitive/inductive crosstalk, the above-described known pulse oximeter structure is modified so that the control unit 14 examines the pulses prior to the actual measurement of blood oxygenation. This is implemented by providing the control unit with timing control means for adjusting the timing of the sampling, i.e. the sampling moment in respect of the pulse edges. As shown in FIG. 4, the control unit first samples the signal with several delays D1 . . . Dn from the leading edge of the pulses (R or IR or both) received and stores the sampled values in its memory. Using the stored data, the control unit can then determine the type and amount of crosstalk prior to the actual measurement. On the basis of this analysis, the control unit can further decide whether the removal of the crosstalk is possible. The pulse oximeter can, for example, first use delay D1 and store the pulse values at sampling moment T1 for a certain period, such as one second (i.e. one sample per pulse is taken over said period). The control unit then adjusts the delay to D2, whereby the pulse values at sampling moment T2 are stored for a period of the same length of time. After several sets of samples have been obtained, a single set i (i=1,2, . . . ) corresponding to delay Di, the control unit has a clear image of the amount and waveform of the crosstalk.

A predetermined rule can be stored in the control unit for determining the presence of crosstalk. To give an example, if the difference between the highest and lowest sample is greater than or equal to a certain threshold value, the control unit decides that crosstalk is present. Further predetermined rules can be stored for evaluating whether crosstalk can be eliminated. These rules may depend on the pulse width used, for example.

Figure 5:
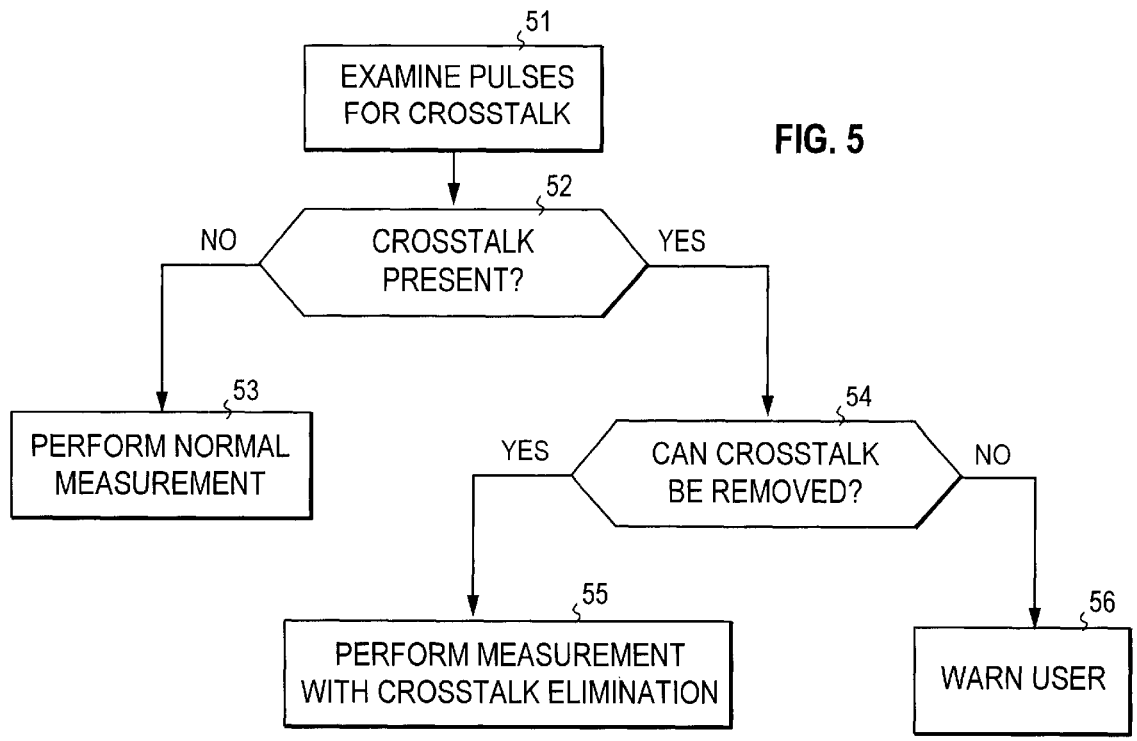
FIG. 5 is a flow diagram showing the operation of the control unit in connection with blood oxygenation measurement.

FIG. 5 illustrates the operation of an embodiment of the pulse oximeter of the present invention. As discussed above, the pulse oximeter first examines the pulses for crosstalk in order to ascertain whether crosstalk is present or not (steps 51 and 52). If it detects that no crosstalk is present in the detector signal, it performs a normal measurement, i.e. determines blood oxygenation in a normal manner (step 53). However, if crosstalk is present, the pulse oximeter evaluates whether it can be removed (step 54). If it detects that crosstalk is so severe that it cannot be removed, a warning is given to the user. However, in a typical case the crosstalk can be removed, in which case the pulse oximeter performs the measurement so that crosstalk has no effect on the result of the measurement (step 55). This can be implemented in various ways as discussed below. If the pulse oximeter detects that the crosstalk can be removed, it can also generate an internal warning signal which is then used to initiate step 55.

Figure 6:
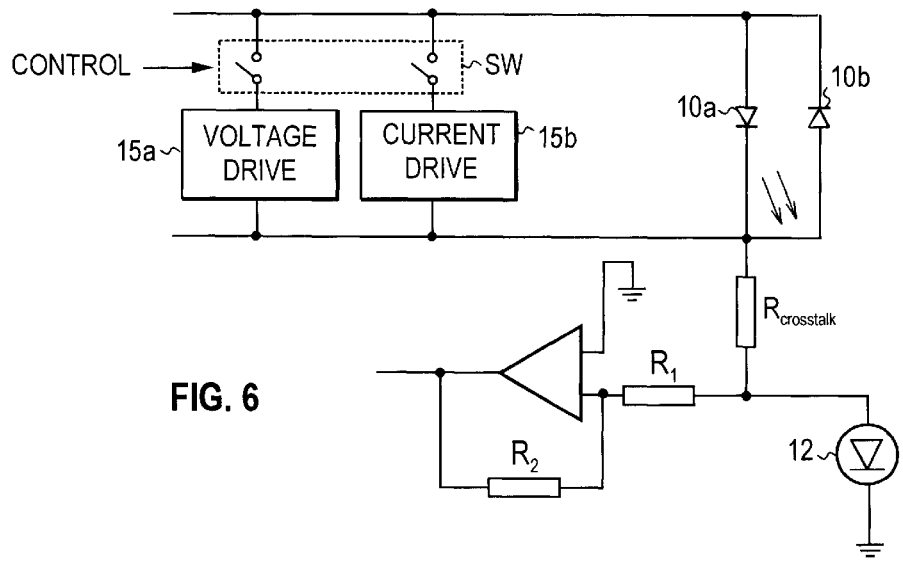
FIG. 6 illustrates an embodiment of the invention intended for detecting resistive crosstalk.

The methods used to detect resistive crosstalk are discussed in the following. As mentioned above, resistive crosstalk causes amplitude changes rather than pulse deformation. The methods for detecting resistive crosstalk are therefore not based on examination of the pulse form. FIG. 6 illustrates the impact of a wet probe in connection with a typical detector circuitry. The crosstalk adds with amplification $R_2/(R_{crosstalk}+R_1)$ the voltage which drives the sending LEDs to the detector signal. This causes error in the detector DC signal, as shown below. Due to this, the pulse oximeter may show higher or lower or equal saturation readings as compared to the correct oxygen saturation of the patient. Patient safety risk is the highest for erroneously high $SpO_2$ readings, which may result, for example, from a positive crosstalk component in the red DC and a negative crosstalk component in the i-red DC.

Figure 7A:
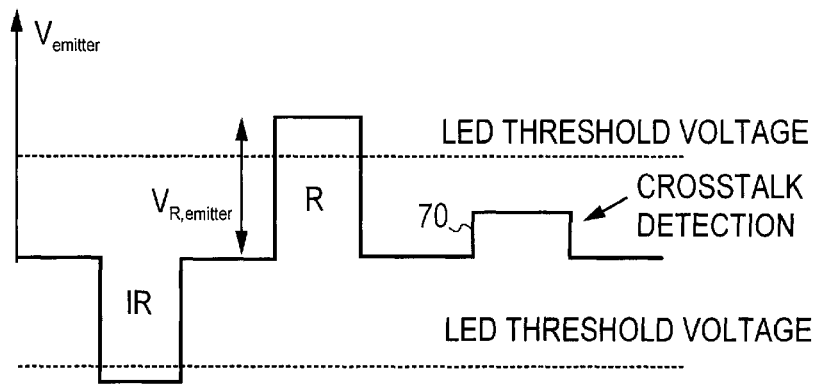
FIGS. 7a to 7c illustrate the detection of resistive crosstalk in the embodiment of FIG. 6.
Figure 7B:
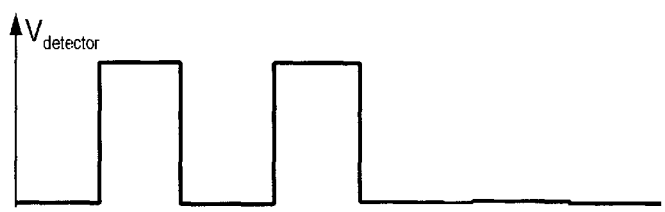
Figure 7C:
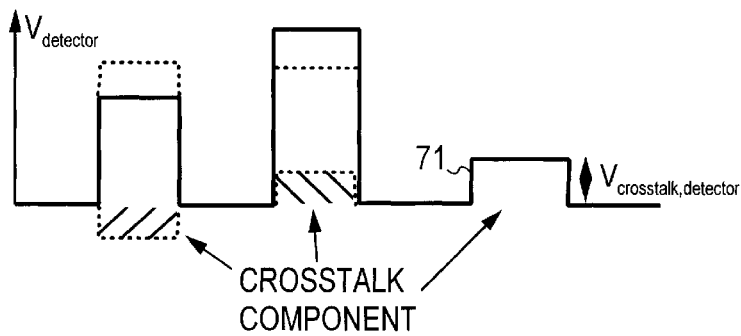

The first method for detecting crosstalk through a leakage resistance is to use a LED drive voltage well below the LED forward voltage threshold needed to light the LED (typically 1 to 3 volts). Since no optical signal is transmitted in this case, any detector signal received is due to leakage (i.e. resistive crosstalk). Thus, in this case the crosstalk is analyzed by driving a LED with a voltage which is below the forward voltage threshold of the LED, and measuring the resulting detector signal. To obtain real-time information of the crosstalk without affecting the $SpO_2$ measurement, the crosstalk detection pulse can be added to the IR and R pulse train driving the LEDs, as shown in FIGS. 7a to 7c. FIG. 7a illustrates the driving pulse train where pulse 70 is added after each IR and R pulse. FIG. 7b shows the corresponding detector voltage when crosstalk is not present and FIG. 7c shows the corresponding detector voltage when crosstalk is present, the crosstalk pulse being denoted with reference numeral 71. As can be seen, the crosstalk component causes a disproportion to appear in the detected amplitudes of the R and IR pulses, since a negative driving pulse (IR) causes a positive pulse but a negative crosstalk component to appear on the detector. When the pulse voltages on the emitter and detector sides are known, the crosstalk component in the R and IR pulses can be removed mathematically according to the following equations:

$$V_{IR, corrected\ detector} = V_{IR, detector} - \frac{V_{IR, emitter}}{V_{crosstalk, emitter}} \times V_{crosstalk, detector}$$

$$V_{R, corrected\ detector} = V_{R, detector} - \frac{V_{R, emitter}}{V_{crosstalk, emitter}} \times V_{crosstalk, detector}$$

where the sign of $V_{IR,emitter}$ will be negative when the actual values are substituted in the equations.

This method thus requires a constant voltage drive, instead of the constant current drive commonly used in pulse oximeters. The transmitting side of the pulse oximeter (the emitter side) is therefore preferably provided with both a constant voltage drive 15a and a constant current drive 15b, as shown in FIG. 6. The control unit selects the voltage or the current mode by controlling the switch SW which connects either one of the drives to the circuit. It is also possible and often practical to measure the LED drive voltage in the constant current drive mode and then to use the measured voltage value to compensate for the crosstalk, whereby no voltage drive mode is needed.

Figure 8A:
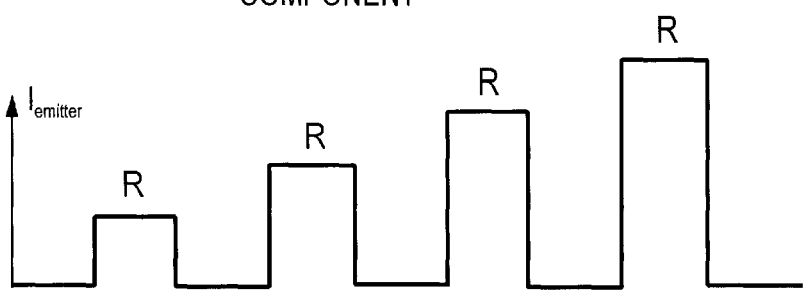
FIG. 8a illustrates a further method of detecting resistive crosstalk.
Figure 8B:
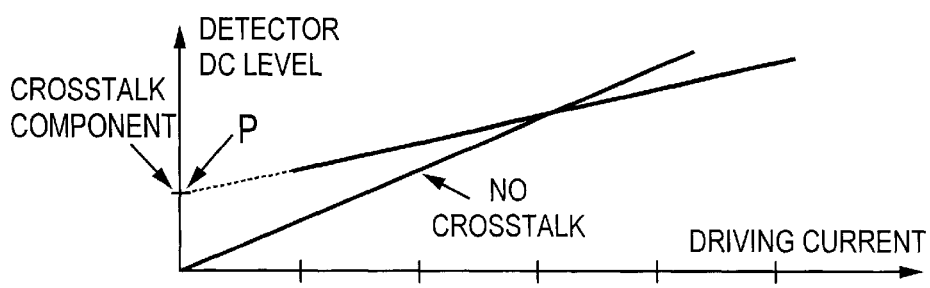
FIG. 8b illustrates the determination of the crosstalk component in the method of FIG. 8a, FIGS. 9 and 10 illustrate two further methods of detecting resistive crosstalk.

The second method for detecting resistive crosstalk is to change the amplitude of the driving current pulses according to a predetermined pattern, preferably linearly, as shown in FIG. 8a. This causes the detector DC signal to also change linearly. Although the optical and crosstalk components of the detector signal cannot be separated from each other, the sum of these components (i.e. the measured detector signal) can be extrapolated to the zero current where no optical signal exists and thereby provide the detector DC level due to crosstalk. This point is denoted by the letter P in FIG. 8b. If there is no crosstalk present, the line of extrapolation should go through the origin. If the extrapolated DC level exceeds a predetermined value, the pulse oximeter decides that crosstalk is present.

If the LED drive supports current adjustment, no hardware modifications are needed and the method can be added to existing pulse oximeters by modifying their controlling software.

Figure 9:
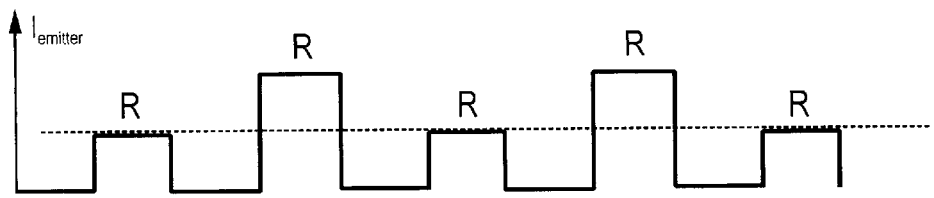

The third method for detecting resistive crosstalk is to modulate the AC component of the driving current pulses, as shown in FIG. 9 (which shows only the R pulses). Thus, in this case an amplitude change repeats in the pulse train (every second pulse of the same type having essentially the same current level). Since the emitted light is proportional to the current that goes through the LEDs, the emitted light should have the same AC to DC ratio as the pulse train. This ratio should be the same on the detector side if no crosstalk appears.

If there is crosstalk present, the AC to DC ratio changes on the detector side because the modulation of the LED current alters the voltage over the LED only a little. This results in a decrease in the AC to DC ratio because the voltage over the LED is fed through from the LED side to the detector side at a nearly constant amplitude. Therefore, when there is crosstalk present, the DC voltage increases or decreases according to the polarity of the crosstalk, but the AC component remains almost unchanged.

This method is primarily used only for detecting resistive crosstalk. If the change in the AC to DC ratio exceeds a certain threshold, the pulse oximeter decides that crosstalk is present. The modulation frequency of the AC component should deviate clearly from the frequency of the physiological signal (i.e. from the patient originated pulsatile component) modulating the pulses.

The fourth method is based on the fact that crosstalk changes the measured $SpO_2$ values. Since the amount of crosstalk is unknown before it is somehow detected, crosstalk cannot be detected on the basis of a single $SpO_2$ reading. However, when the DC light on the LED side changes, the voltage over the LEDs changes a little as well. The change in the DC light should not affect the (known) modulation ratio $R=[(AC_R)/DC_R)/(AC_{IR}/DC_{IR})]$, unless crosstalk exists. If the change in R exceeds a certain threshold, the pulse oximeter decides that crosstalk is present.

The above first method of detecting resistive crosstalk offers real-time measurement, since the detection pulses 70 are added to the pulse sequence driving the LEDs, while the second, third, and fourth methods require an inadvance crosstalk measurement prior to the actual $SpO_2$ measurement. The crosstalk measurement preceding the actual measurement lasts typically a few seconds at most. On the other hand, the second, third, and fourth methods require no hardware changes in the pulse oximeter, but only changes in the controlling software of the control unit in order to allow the driving current to be controlled according to the respective method. The first method is the most suitable for removing crosstalk, since the hardware can be designed by taking the removal of crosstalk into account. The second, third, and fourth methods are in turn primarily for the purpose of crosstalk detection, since in practice the hardware of existing pulse oximeters is not designed for the above methods. Therefore, if one of the above methods is to be introduced into a new pulse oximeter model, the first method is the preferred one.

Figure 10:
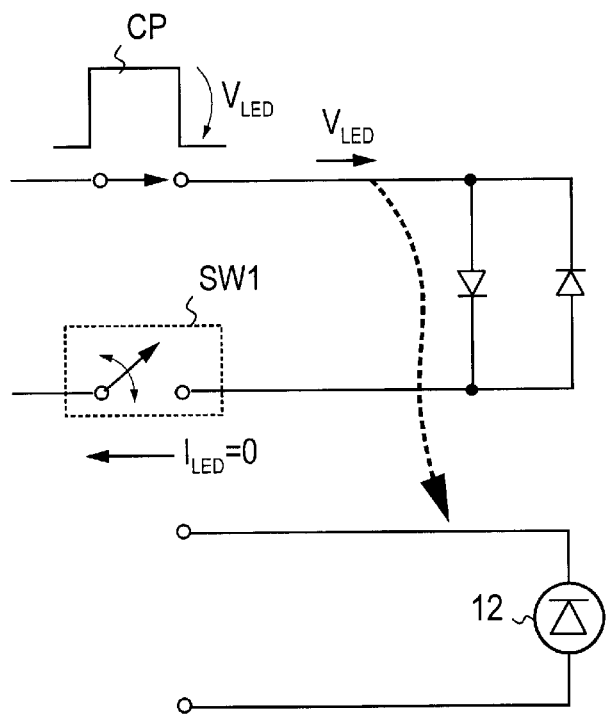

FIG. 10 illustrates a further method for detecting crosstalk through a leakage resistance, the method being analogous to the above-described first method in the sense that a LED is driven without the transmission of an optical signal. In this method, one of the wires of a LED is activated to a drive voltage and a second one is kept in a floating state so as not to cause current to pass through the LED. This can be accomplished, for example, by disconnecting a switch SW1 located at some point along the said other wire simultaneously when the voltage pulse is supplied. Since no optical signal is transmitted, any substantial change in the detector signal can be interpreted as crosstalk. Similarly to FIGS. 7a to 7c, the crosstalk detection pulses CP can be in the pulse train driving the LEDs in order to obtain real-time information about the crosstalk without affecting the $SpO_2$ measurement. The switch is then disconnected for the duration of the said pulses in order to detect whether crosstalk is present. Since the implementation of this method requires that a controllable switch (SW1) be installed in the current pulse oximeters, the method requires both hardware and software changes.

Figure 11:
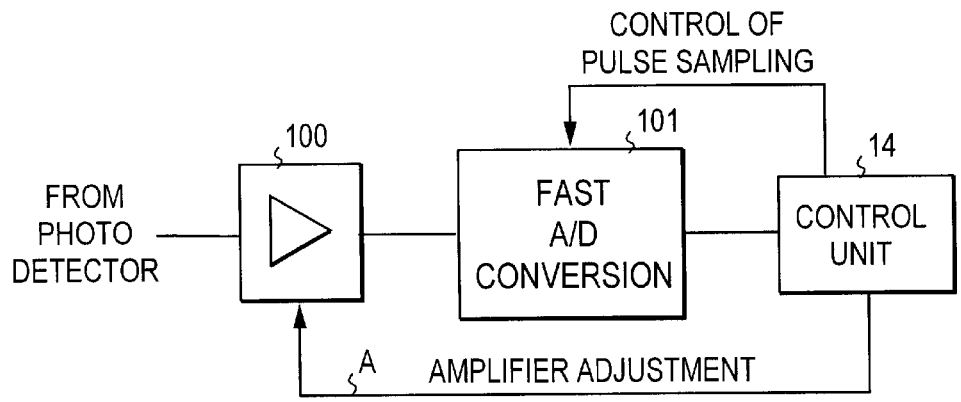
FIG. 11 shows a pulse oximeter according to a further embodiment of the invention.

FIG. 11 illustrates a pulse oximeter according to another embodiment of the invention. This embodiment is based on a fast A/D conversion. The signal received from the photodetector and amplified in an amplifier stage 100 is read directly by a fast A/D converter 101. The resulting digitized data stream is supplied to the control unit. The sampling rate of the converter is typically about 50 k samples/s (thus resulting in about 100 samples per pulse), which allows an accurate estimation of the pulse shape to be stored in the control unit. The embodiment based on the fast A/D conversion is therefore especially suitable for detecting and removing capacitive/inductive crosstalk and analyzing the type of the crosstalk, although it is suitable for detecting and removing resistive crosstalk too.

As discussed above, according to the present invention the signal received from the photodetector is analyzed in order to detect whether crosstalk is present or not. The blood oxygenation measurement is then performed so that crosstalk has no effect on the result of the measurement, at least whenever possible.

In order to obtain crosstalk-free results, the crosstalk detected can be removed mathematically by the control unit. This applies especially to pulses where the overshoot is exponential (capacitive crosstalk) but small. Thus in this case step 55 of FIG. 5 comprises two phases: (1) measuring blood oxygenation in a normal manner and (2) removing the crosstalk mathematically from the digitized signal. Various rules can be used for detecting the presence of crosstalk and for eliminating it.

Secondly, crosstalk can be removed by carrying out measurements so that the crosstalk has no effect on the values of the samples. In other words, the sampling moment can be selected so that the overshoot has decayed. This applies especially to ringing (capacitive-inductive crosstalk). If necessary, the pulse width can be increased to allow the overshoot decay. Thus, in this case the control unit controls the timing of the sampling units (32, 33) and possibly also widens the pulses so that crosstalk is not present at the sampling moment.

Thirdly, the above methods of removal can be combined. For example, if the pulses are very narrow and the crosstalk cannot be removed mathematically, the pulses can be widened only to the extent necessary for making mathematical removal possible.

The detection of crosstalk can also be performed for other purposes than the direct and automatic elimination of crosstalk. For example, the pulse shape detected can be used to detect the type of the cable and/or probe used, and warn the user of a wrong type. Alternatively, if excessive capacitive or resistive crosstalk is detected, the user can be warned of a faulty or dirty probe. A faulty probe typically shows in the pulse form, whereas a dirty probe shows in excessive resistive crosstalk. In response to the crosstalk detected, the pulse oximeter can also automatically adjust the amplifier circuitry so that crosstalk is minimized. If the pulse oximeter detects excessive crosstalk, it can try different amplifier configurations in order to find the one that optimally minimizes crosstalk. If the pulse oximeter detects that the excessive crosstalk is due to a certain type of cable, such as a coaxial cable, it can adjust the amplifier circuitry so that it is more suitable for such a cable. This possibility is illustrated in FIGS. 3 and 11 by arrows A. Instead of the reconfiguration of the amplifier circuitry, or in addition to it, the pulse oximeter can ground the shield of the coaxial cable used.

Although the invention was described above with reference to the examples shown in the appended drawings, it is obvious that the invention is not limited to these, but may be modified by those skilled in the art without departing from the scope and spirit of the invention. For example, the pulse oximeter can be provided with more than two wavelengths. Furthermore, the method can also be used in other devices than pulse oximeters, the devices measuring other substances in a similar manner, i.e. non-invasively by radiating the patient. An example of such measurement is the determination of the amount of glucose in the tissue of a patient.

What is claimed is:

1. A method for detecting the validity of measurement circumstances in connection with a monitoring device intended for determining the amount of at least one light absorbing substance in a subject, the monitoring device comprising emitters for emitting radiation at a minimum of two wavelengths, driving means for activating said emitters, and a detector for receiving said radiation at said wavelengths and for producing an electrical signal in response to the radiation, the method comprising the steps of:

providing a drive signal to an emitter, the drive signal traveling in a direction to said emitter and having predetermined characteristics;

analyzing an electrical signal, traveling in a direction from a detector, in timed relation to said drive signal in order to detect whether a crosstalk component caused by electric power coupled directly from said drive signal is present in said electrical signal, said crosstalk component resulting from at least one of capacitive, inductive and resistive power coupling from said drive signal to said electrical signal; and, taking predetermined measures when said crosstalk component is detected.

2. A method according to claim 1, wherein said analyzing step includes sampling the electrical signal and analyzing the samples obtained.

3. A method according to claim 2, wherein said sampling step includes:

sampling the electrical signal by a synchronous detector, taking one sample per each pulse of the electrical signal; and shifting the sampling moments so that samples of the pulses are obtained at different points for ascertaining the waveform of the pulses.

4. A method according to claim 2, wherein said sampling step includes sampling the electrical signal by an A/D converter, taking a plurality of samples per each pulse of the electrical signal.

5. A method according to claim 3 or 4, wherein the step of taking the predetermined measures includes generating a measurement signal essentially void of said crosstalk component.

6. A method according to claim 5, wherein said generating step includes removing the crosstalk component mathematically.

7. A method according to claim 5, wherein said generating step includes adjusting the sampling moments on the basis of said samples in order to allow the crosstalk component to disappear from the electrical signal; and, generating the measurement signal by sampling the electrical signal at the adjusted sampling moments.

8. A method according to claim 5, wherein said generating step includes:

adjusting the pulse width of the drive signal; and, generating the measurement signal by sampling the electrical signal resulting from the drive signal with the adjusted pulse widths.

9. A method according to claim 5, wherein said generating step includes changing the configuration of an amplifier stage amplifying the electrical signal.

10. A method according to claim 5, wherein said generating step includes grounding the shield of a cable containing the electrical signal.

11. A method according to claim 1, wherein said analyzing step includes determining the type of the crosstalk.

12. A method according to claim 1, wherein the step of taking the predetermined measures includes producing a warning of impending measurement errors when the electrical signal fulfills predetermined criteria.

13. A method according to claim 12, wherein:

the drive signal comprises voltage pulses, the amplitude of which is insufficient to activate said at least one emitter; and, said producing step includes creating the warning when the amplitude of the electrical signal exceeds a predetermined threshold during said voltage pulses.

14. A method according to claim 12, wherein the drive signal includes current pulses of different amplitudes.

15. A method according to claim 14, further comprising the steps of:

storing the values of the electrical signal corresponding to said different amplitudes; and, estimating an electrical signal value of the electrical signal corresponding to a zero amplitude current pulse using said stored values;

wherein the warning is generated when the estimated electrical signal value exceeds a predetermined threshold value.

16. A method according to claim 14, further comprising the step of modulating an AC component of the current pulses, the warning being generated when an AC to DC ratio of the electrical signal deviates essentially from that of the drive signal.

17. A method according to claim 14, further comprising changing of a DC level of the drive signal.

18. A method according to claim 12, wherein:

the drive signal comprises a voltage pulse, the amplitude of which is sufficient to activate said at least one emitter; and said driving step includes preventing current from flowing through said at least one emitter during said voltage pulse, thereby preventing the emitter from generating radiation, the warning being produced when the amplitude of the electrical signal exceeds a predetermined threshold during said voltage pulse.

19. A method according to claim 12, wherein the warning is given to the device itself.

20. A method according to claim 12, wherein the warning is given to a user of device itself.

21. A method according to claim 1, wherein the amount of at least one light absorbing substance is determined in the blood of a subject.

22. A method according to claim 1, wherein the monitoring device is a pulse oximeter.

23. An apparatus for non-invasively determining the amount of at least one light absorbing substance in a subject, the apparatus comprising:

emitters for emitting radiation at a minimum of two different wavelengths;

driving means for providing a drive signal to said emitters, the drive signal traveling in a direction to said emitters and having predetermined characteristics, wherein said emitters are activatable to emit said radiation, a detector for receiving said radiation at said wavelengths, wherein an electrical signal traveling in a direction from said detector includes at least a portion in response to the received radiation;

sampling means for sampling the electrical signal, whereby a sampled signal is obtained;

signal processing means for determining said amount by processing the sampled signal; and crosstalk detection means for analyzing the electrical signal in timed relation to the drive signal in order to detect whether a crosstalk component being caused by electric power coupled directly from said drive signal is present in said electrical signal, said crosstalk component resulting from at least one of capacitive, inductive and resistive power coupling from the drive signal to the electrical signal.

24. An apparatus according to claim 23, further comprising crosstalk elimination means for generating a measurement signal essentially void of said crosstalk component.

25. An apparatus according to claim 24, wherein:
the sampling means comprise a synchronous detector adapted to take one sample per each pulse of the electrical signal; and
the crosstalk elimination means are adapted to adjust the sampling moment so that the samples are obtained at pulse points where the crosstalk component is substantially negligible.

26. An apparatus according to claim 24, wherein:
the sampling means comprise an A/D converter taking a plurality of samples per each pulse of the electrical signal; and
the crosstalk detection means and the crosstalk elimination means are part of the signal processing means.

27. An apparatus according to claim 23, wherein the driving means comprise at least one of the following:
a current drive adapted to output current pulses of different amplitudes for activating the emitters; and,
a voltage drive adapted to output voltage pulses the amplitude of which is insufficient to activate the emitters.

28. An apparatus according to claim 23, wherein:
the driving means are adapted to (1) supply voltage to one lead of an emitter, and (2) simultaneously prevent current from flowing through said emitter, thereby preventing the emitter from generating radiation.

29. An apparatus according to claim 28, wherein the driving means are adapted to disconnect another lead of said emitter, thereby preventing current from flowing.

30. An apparatus according to claim 23, said apparatus being a non-invasive pulse oximeter.

31. A method for detecting the validity of measurement circumstances in connection with a monitoring device intended for determining the amount of at least one light absorbing substance in a subject, the monitoring device comprising emitters for emitting radiation at a minimum of two wavelengths, driving means for activating said emitters, and a detector for receiving said radiation at said wavelengths and for producing an electrical signal in response to the radiation, the method comprising the steps of:

driving an emitter by a drive signal traveling in a direction to the emitter and including one of the following pulses:
voltage pulses, the amplitude of which is insufficient to activate the emitter; and,
current pulses of different amplitudes;

analyzing an electrical signal traveling in a direction from the detector;

detecting a crosstalk component caused by electric power coupled directly from said drive signal, using at least one of the following checks:
checking whether the amplitude of the electrical signal exceeds a predetermined threshold during said voltage pulses; and,
checking whether the amplitude of the electrical signal exceeds another predetermined threshold during said current pulses when the amplitude of said current pulses is zero; and, taking predetermined measures when said crosstalk component is detected.

32. A method according to claim 31, wherein the step of taking the predetermined measures includes producing a warning of impending measurement errors when the electrical signal fulfills predetermined criteria.

33. A method according to claim 32, wherein the drive signal includes current pulses of different amplitudes and further comprising the steps of:
storing the values of the electrical signal corresponding to said different amplitudes; and
estimating an electrical signal value corresponding to a zero amplitude current pulse using the stored values;
wherein the warning is generated when the estimated value exceeds a predetermined threshold value.

34. A method according to claim 32, further comprising the step of modulating an AC component of the current pulses, the warning being generated when an AC to DC ratio of the electrical output signal deviates essentially from that of the drive signal.

35. A method according to claim 32, further comprising changing of a DC level of the drive signal.

36. A method according to claim 31, wherein:
the drive signal comprises a voltage pulse, the amplitude of which is sufficient to activate said at least one emitter; and,
said driving step includes preventing current from flowing through said at least one emitter during said voltage pulse, thereby preventing the emitter from generating radiation, the warning being produced when the amplitude of the electrical signal exceeds a predetermined threshold during said pulse.

37. An apparatus for non-invasively determining the amount of at least one light absorbing substance in a subject, the apparatus comprising:
emitters for emitting radiation at a minimum of two different wavelengths;
driving means for activating said emitters by a drive signal, said drive signal including one of the following pulses:
voltage pulses, the amplitude of which is insufficient to activate said emitters; and,
current pulses, the amplitude of which is zero at least once; and,
a detector for receiving said radiation at said wavelengths and producing an electrical signal in response to the radiation;

sampling means for sampling the electrical signal, whereby a sampled signal is obtained;

signal processing means for determining said amount by processing the sampled signal; and crosstalk detection means for analyzing whether a direct electric crosstalk component is present in the electrical signal, the direct electric crosstalk component being caused by electric power coupled directly from said driving means to said electrical signal, said analysis including at least one of the following checks:

whether the amplitude of the electrical signal exceeds a predetermined threshold during said voltage pulses; and, whether the amplitude of the electrical signal exceeds another predetermined threshold during said current pulses when the amplitude of said current pulses is zero.

38. An apparatus according to claim 37, wherein the driving means comprise at least one of the following:

a current drive adapted to output current pulses for activating the emitters; and, a voltage drive adapted to output voltage pulses the amplitude of which is insufficient to activate the emitters.

39. An apparatus according to claim 37, wherein the driving means are adapted to (1) supply voltage to one lead of an emitter and (2) simultaneously prevent current from flowing through said emitter, thereby preventing the emitter from generating radiation.

40. An apparatus according to claim 39, wherein the driving means are adapted to disconnect another lead of said emitter, thereby preventing current from flowing.

41. An apparatus according to claim 37, said apparatus being a non-invasive pulse oximeter.

* * * * *

UNITED STATES PATENT AND TRADEMARK OFFICE
CERTIFICATE OF CORRECTION

PATENT NO.    : 6,963,767 B2  
DATED         : November 8, 2005  
INVENTOR(S)   : Rantala et al.

Page 1 of 1

It is certified that error appears in the above-identified patent and that said Letters Patent is hereby corrected as shown below:

<u>Column 10,</u>
Line 59, delete "itself".

Signed and Sealed this

Seventh Day of March, 2006

JON W. DUDAS  
*Director of the United States Patent and Trademark Office*